(12) United States Patent
Shyu et al.

(10) Patent No.: US 8,777,860 B2
(45) Date of Patent: Jul. 15, 2014

(54) METHOD FOR EVALUATION OF RENAL VASCULAR PERFUSION USING POWER DOPPLER ULTRASONOGRAPHY

(75) Inventors: Jeou-Jong Shyu, Taipei (TW); Sun-Hua Pao, Taipei (TW); Yio-Wha Shau, Taipei (TW); Shuo-Meng Wang, Taipei (TW); Nai-Kuan Chou, Taipei (TW)

(73) Assignee: National Taiwan University, Taipei (TW)

( * ) Notice: Subject to any disclaimer, the term of this patent is extended or adjusted under 35 U.S.C. 154(b) by 1207 days.

(21) Appl. No.: 12/646,753

(22) Filed: Dec. 23, 2009

(65) Prior Publication Data

US 2010/0274134 A1 Oct. 28, 2010

(30) Foreign Application Priority Data

Apr. 23, 2009 (TW) ................................. 98113514 A

(51) Int. Cl.
*A61B 8/00* (2006.01)
*G06T 7/00* (2006.01)
*A61B 8/06* (2006.01)
*A61B 8/13* (2006.01)
*A61B 18/00* (2006.01)
*A61B 5/20* (2006.01)

(52) U.S. Cl.
CPC ...... *G06T 7/0016* (2013.01); *A61B 2018/00511* (2013.01); *A61B 5/201* (2013.01); *A61B 8/06* (2013.01); *A61B 8/13* (2013.01); *A61B 8/469* (2013.01); *G06T 2207/10016* (2013.01); *G06T 2207/10132* (2013.01); *G06T 2207/20104* (2013.01); *G06T 2207/30084* (2013.01); *G06T 2207/30104* (2013.01)
USPC ............................. 600/454; 600/438; 382/128

(58) Field of Classification Search
None
See application file for complete search history.

(56) References Cited

U.S. PATENT DOCUMENTS

| | | | | |
|---|---|---|---|---|
| 5,860,929 | A * | 1/1999 | Rubin et al. | 600/454 |
| 8,047,993 | B2 * | 11/2011 | Shau et al. | 600/453 |
| 2003/0236460 | A1 * | 12/2003 | Ma et al. | 600/441 |
| 2007/0078344 | A1 * | 4/2007 | Rafter | 600/450 |

OTHER PUBLICATIONS

JH Young, MJ Klag, P Muntner, JL Whyte, M Pahor, J Coresh. "Blood Pressure and Decline in Kidney Function: Findings from the Systolic Hypertension in the Elderly Program." Journal of the American Society of Nephrology 13(11): 2776-2782. Nov. 1, 2002.*
Yio-Wha Shau, et al, Renal Vascular Perfusion Index in a Canine Model, Journal, Ultrasound in Med. & Biol. vol. 35, No. 1, pp. 36-43, 2009.

* cited by examiner

*Primary Examiner* — Unsu Jung
*Assistant Examiner* — Amanda Lauritzen Moher
(74) *Attorney, Agent, or Firm* — WPAT, P.C.; Anthony King

(57) ABSTRACT

A method for evaluation of renal perfusion with power Doppler ultrasonography is disclosed in the present invention. Serial renal vascular images at different vascular areas including the whole vascular tree, interlobar, arcuate, and interlobular vessels were captured. Imaging processing software was designed to analyze the changes of power Doppler intensity of colored pixels within regions of interest (ROI). Power Doppler Vascularity index (PDVI) has been defined as the percentage of vascular perfusion within a region of interest (ROI). The renal vascular perfusion index (RVPI) is defined as the maximal power Doppler vascular index divided by minimal power Doppler vascular index ($PDVI_{max}/PDVI_{min}$) among the serial images. The mean of weighted power Doppler vascular index ($WPDVI_{mean}$) is defined as the average of the intensity of color pixels among the ROI within the serial images. By using the RVPI and $WPDVI_{mean}$, a more dynamic sense of vascular perfusion and a novel approach for the evaluation of renal vascular function in clinical practice can be provided.

13 Claims, 18 Drawing Sheets
(15 of 18 Drawing Sheet(s) Filed in Color)

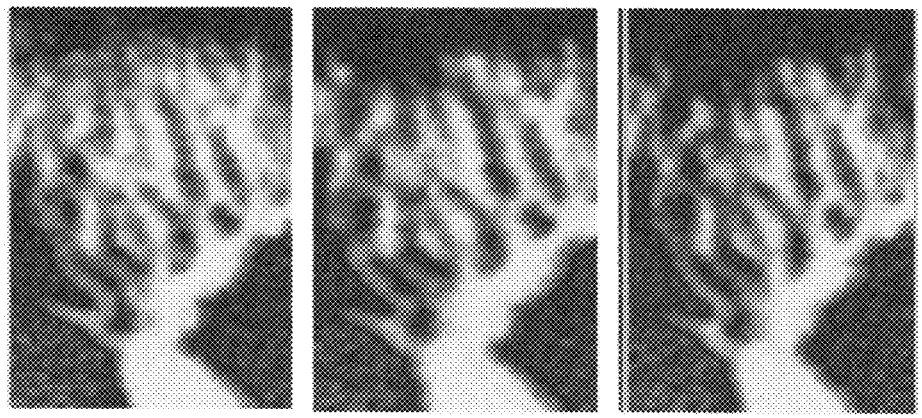
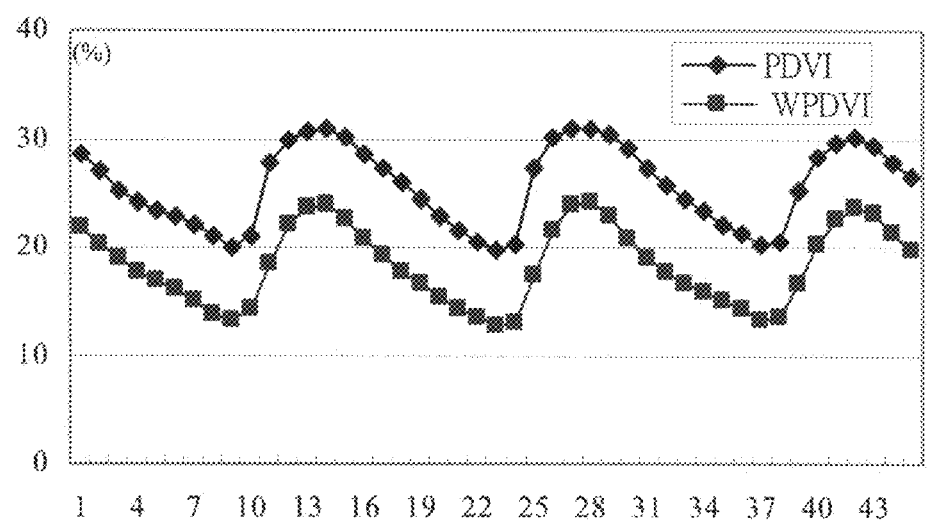
Fig. 10E (Frame No.)

METHOD FOR EVALUATION OF RENAL VASCULAR PERFUSION USING POWER DOPPLER ULTRASONOGRAPHY

BACKGROUND OF THE INVENTION

1. Field of the Invention

The present invention relates to a method for evaluation of renal perfusion, in particular to a method for evaluation of renal perfusion by capturing and analyzing consecutive serial images in renal vessels using power Doppler ultrasonography.

2. The Prior Arts

The main function of kidney is to remove metabolic wastes (mainly nitrogenous wastes) in the body. Declines in renal function may accumulate metabolite wastes in the body and consequently cause multiple-organ dysfunction or even death unless renal dialysis treatment or kidney transplantation is performed. A large amount of blood flow supply is necessary for the renal function, so that 25~40% cardiac output comes into kidney for the renal perfusion. Therefore the measurement of renal blood flow has become an important tool for the assessment of renal functions. Power Doppler ultrasonography provides a non-invasive method among the various measurement methods of renal perfusion. In the past, renal perfusion examined with power Doppler was explained by a single image from the large renal area with an image of best perfusion. However the clinical application is limited. Because the heart has dynamic blood flow to reach the kidney via aorta. It's difficult to elucidate the dynamic blood flow state with a static image.

Early detection of renal problems is beneficial for proper treatment. During the last decade, both color Doppler and power Doppler sonography have been widely used to evaluate renal functions. Unlike computer tomography (CT) scans and magnetic resonance imaging (MRI), color Doppler images, based on the mean Doppler frequency shift induced by blood flow velocity, easily present the overall renal vascular structure, as well as the flow direction and velocity. However, color Doppler is not sensitive in depicting small vessels or vessels with low velocity. Power Doppler sonography is based on the total integrated energy of Doppler shifted echoes and has higher sensitivity for much slower blood flow, but it can not address the flow direction or flow velocity. Lately, a directional power Doppler imaging mode has been implemented in commercially available duplex ultrasound systems in which the positive and negative flows are separated before the estimation of Doppler strength. The flow direction is encoded in the power Doppler image with a two-color scale which showed some clinical applications.

Pulsed Doppler ultrasound clinically measures vascular resistive index (RI), pulsatility index (PI) and systole/diastole ratio through blood flow velocity, which shows the renal vascular resistance and is often used to estimate the changes of flow velocity. The traditional S/D ratio, RI or PI measured using pulse Doppler imaging can only depict the flow at the interlobar vessels and at most down to the size of arcuate vessels. In addition, these methods showed poor specificity and sensitivity.

Previously, Power Doppler was applied to examine vascular structure of the renal cortex (areas covered by arcuate vessels and interlobular vessels), such as to detect renal vascular perfusion in pigs after administration of adrenocorticotropic hormone and papaverine. Power Doppler was also applied to detect impaired perfusion in acute pyelonephritis, and to identify cases of acute or chronic vascular rejection with interlobular vascular signal after renal transplantation. However, all these applications collected "static" information on renal perfusion without details on haemodynamics, which were not sufficient to reflect the actual dynamic condition of renal perfusion.

SUMMARY OF THE INVENTION

To solve the foregoing disadvantages present in the prior art, the object of the present invention is to provide a non-invasive evaluation method for examination of renal perfusion using Power Doppler ultrasonography to detect the real-time status of renal perfusion, and to provide a more dynamic, haemodynamic-matching information for quantification of renal perfusion and evaluation of renal function.

The techniques of the present invention principally comprises the steps of: using a Power Doppler ultrasound and consecutively capturing serial images on kidney; selecting a region of interest (ROI) for vascular analyses; demarcating and summing pixels showing reflected signals of blood flow to obtain the area of blood perfusion per image; and calculating the ratio of the quantity of the pixels having reflected signals of blood flow to the total of pixels in the ROI to obtain a power Doppler vascularity index (PDVI). Based on the defined PDVI of each image, a curve that lasted for at least two heartbeat cycles was plotted. The ratio of maximal and minimal values in the PDVI curves was calculated and defined as a renal vascular perfusion index (RVPI). Besides, since the brightness of pixels having reflected signals of blood flow may varies with the amount of blood perfusion, they were normalized against the maximal brightness value. The ratio of the weighted value to the ROI is defined as color-weighted power Doppler vascular index (WPDVI). The mean of the WPDVIs calculated from all images is defined as a mean color-weighted power Doppler vascular index (WPDVImean). Moreover, the WPDVI waveform of the original ROI was used to calculate the correlation matrix with the local waveform of scatter strength to establish the power Doppler blood flow correlation-map.

The present invention provides a non-invasive, inclusive of complete heartbeat cycles, dynamic, haemodynamic-matching analysis method using the power Doppler ultrasound. The curves obtained by the method according to the present invention show a regular pattern. In addition, the accuracy of quantification of renal perfusion and evaluation of renal function is greatly enhanced with the use of WPDVI in combination with PDVI.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4b shows PDVI waveforms corresponding to four regions of FIG. 4a;

FIGS. 10a to 10f reveal renal vascular perfusion monitored under various conditions in human clinical trial.

DETAILED DESCRIPTION OF THE PREFERRED EMBODIMENT

To enable persons skilled in the art to better understand the aforementioned objective, features and advantages of the present invention, embodiments are quoted and explained in combination with attached Figs. as follows.

The present invention relates to a method for quantification of renal perfusion using power Doppler ultrasonography. The techniques of the invention principally comprises the steps of: using a Power Doppler ultrasound and consecutively capturing serial images (n=45) on kidney for at least two complete heartbeat cycles; selecting a region of interest (ROI) for vascular analyses; demarcating and summing pixels showing reflected signals of blood flow to obtain the area of blood perfusion per image; and calculating the ratio of the quantity of the pixels having reflected signals of blood flow to the total of pixels in the ROI to obtain a power Doppler vascularity index (PVDI). Based on the defined PVDI of each image, a curve that lasted for at least two heartbeat cycles was plotted. The ratio of the maximal (the maximal systole) and the minimal values (the minimal diastole) was calculated and defined as a renal vascular perfusion index (RVPI), i.e. RVPI=$PDVI_{max}$/$PDVI_{min}$.

Clinical ultrasound ATL HDI 5000 with a 5-12 MHz linear array transducer was used for capturing two-dimensional power Doppler ultrasonographic images in the present invention. The scan pattern were set at fixed parameters for wall filter, color power angio (CPA) and pulsed repetition frequency (PRF) in order to ensure a stable performance. Taking HDI-5000 as an example, the wall filter was set at the "medium", which is about 1.5 cm/sec for the flow velocity; CPA was set at 81%; and PRF was suggested to set at 1000 Hz, for lower value increased the sensitivity of the blood flow measurement. The images captured from the longitudinal sections and the cross sections of kidney were invariably captured after scanned with an ultrasonic probe and subsequently downloaded in DICOM (digital image for communication in medicine) format with 45 frames each time. The images having the graphical quality of 24-bit color and 640×476 pixels were collected thru internet and stored in personal computer for future analysis. The Renal Vascularity Index Quantification software written in Borland C++ Builder as platform (designed by the inventor) was used for analysis. To correct for breathing and body movements, the viewing window in sequential frames were carefully realigned using 2D image auto-correlation of selected grey-scale land-marks in the sonogram. The image shift was corrected by convoluting the pixel positions of continuous images with the corresponding brightness to search the maximal correlation coefficient for correction. The serial images were adjusted in parallel but neglected the rotation and deformation effects in order to increase the calculating efficiency.

Figure 1:
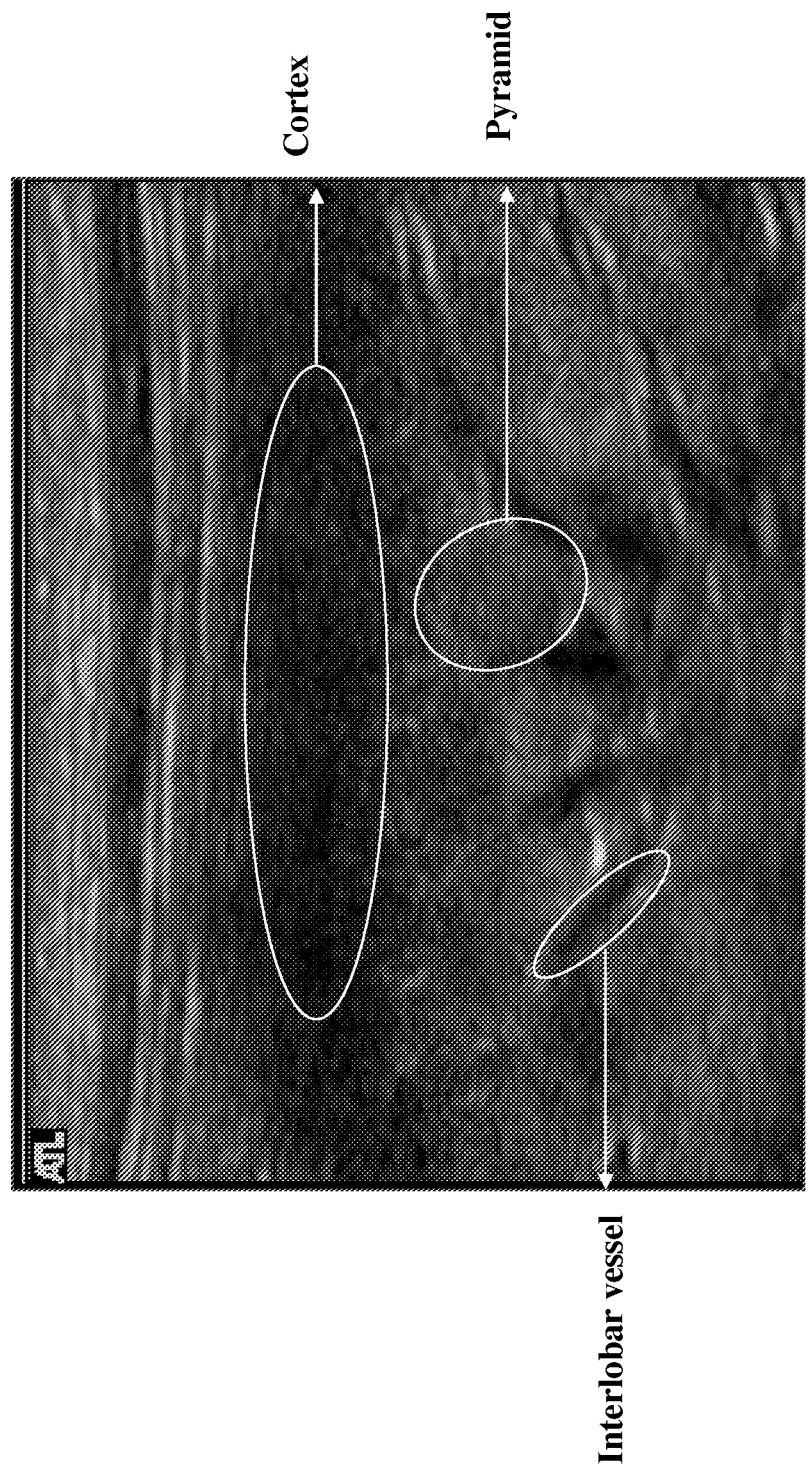
FIG. 1 shows the shape of whole kidney, the cortex, the medulla, the pyramid and the pelvis examined with a B-mode scan.
Figure 2:
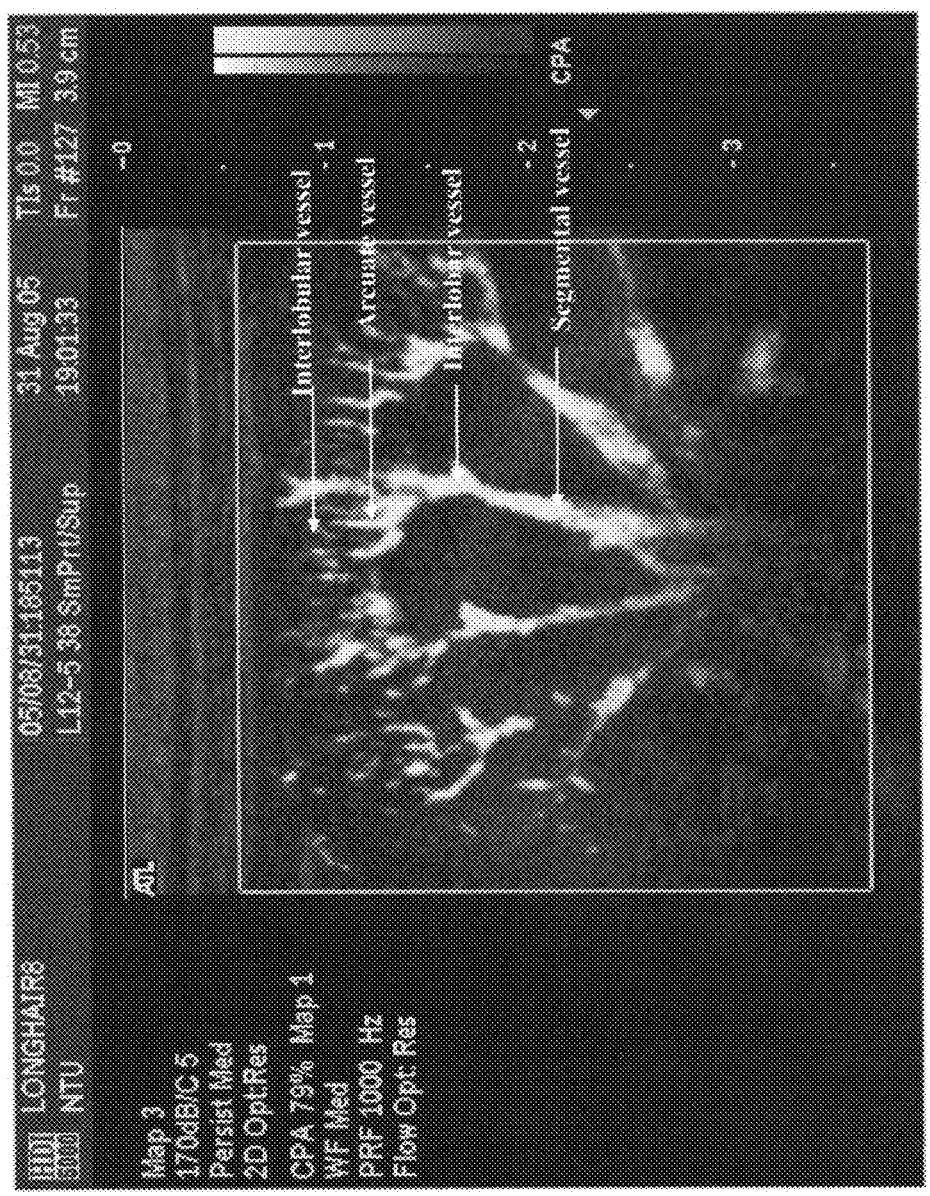
FIG. 2 shows blood flow images in various renal vessel areas using power Doppler ultrasonography.

Referring to FIG. 1, a B-mode scan was performed to examine the whole kidney, followed by the cortex, the medulla, the pyramid, the pelvis and so on prior to analysis of renal vascular perfusion. The region between the pelvis and the medulla was found, and then the cortical region. Both color Doppler and power Doppler sonograms were used to examine the blood flow in those selected areas. Color Doppler could detect different directions of blood flow in arteries and veins with more noises, whereas Power Doppler could detect the blood flow in finer vessels. Since Power Doppler does not display flow, the blood flow of arteries and veins was included in the images. The whole vascular distribution was shown in FIG. 2. During examination of renal blood flow with Power Doppler and subsequent data collection, the images of vascular tree including interlobar, arcuate and interlobular vessels should be selected in the region of ROI, and successive images were observed. Images with clear resolution and smallest noise were selected and saved in DICOM format. Multiple files of vascular trees at different sites and in different regions were saved for each examination. The data was predominantly saved as Power Doppler images for further analysis.

Figure 3:
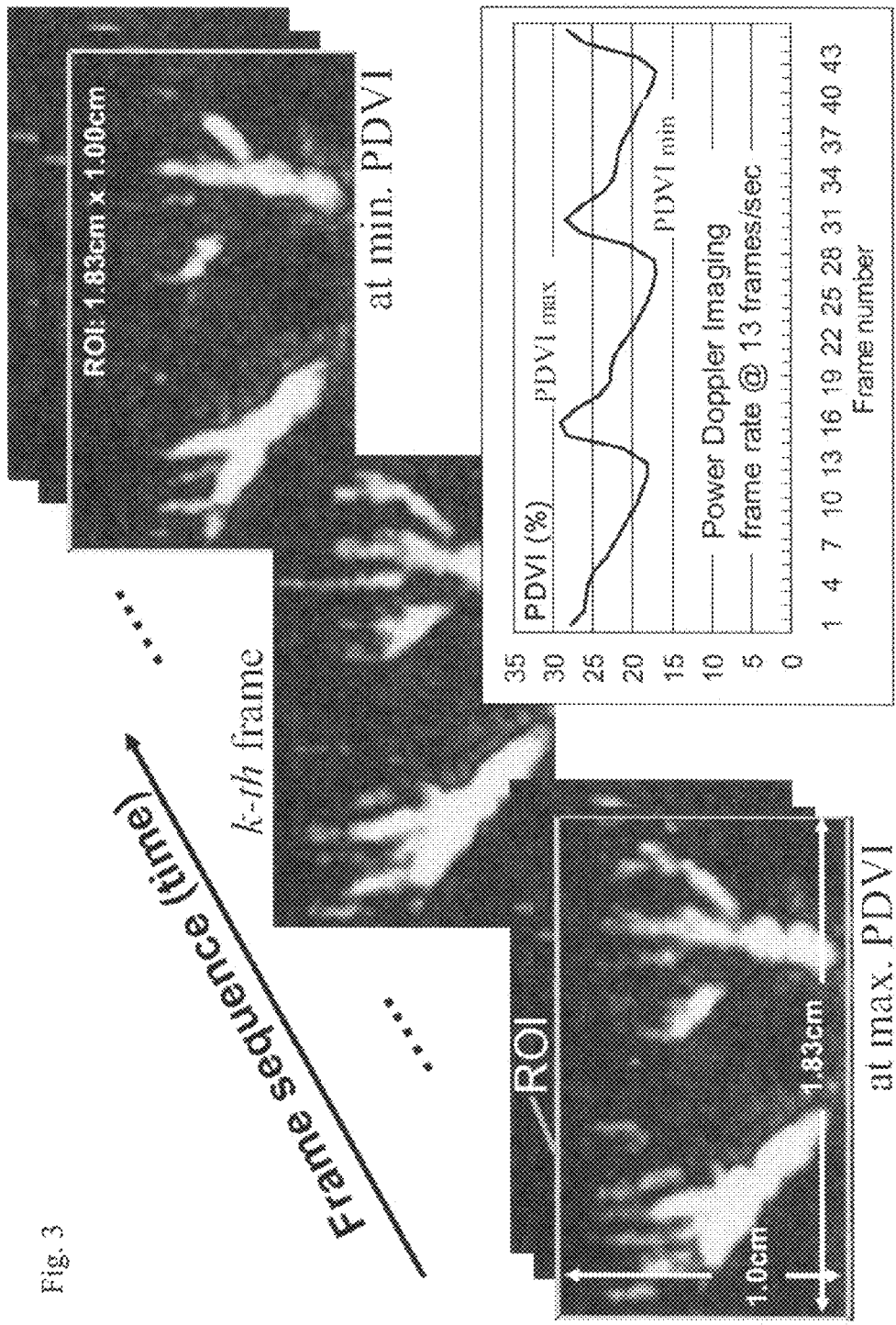
FIG. 3 shows analysis on serial images of renal vascular tree captured with power Doppler.

Power Doppler Vascularity index (PDVI) in the present invention was defined as the percentage of blood perfusion area within a region of interest (ROI). The mathematical expression is:

$$PDVI^k = \frac{1}{A_{ROI}} \cdot \sum_{i=1}^{nx} \sum_{j=1}^{ny} I_{i,j}^k \qquad (1)$$

$$(k = 1, N)$$

where superscript k is the frame index of consecutive images, N is the total number of frames (N=45), and nx and ny are the width and height of the ROI for the i-th row and j-th column respectively. $A_{ROI}$ is the total number of pixels in the ROI and $I_{i,j}$ is the binary-coded matrix from the digitalized image; where $I_{i,j}$=1 for colored pixels otherwise $I_{i,j}$=0. FIG. 3 shows the typical power Doppler sequential images of the renal vascular tree (ROI: 1.00 cm×1.83 cm; nx: 230; ny: 126). With a power Doppler imaging frame rate of 13 Hz, the percentage of colored pixels in the ROI (i.e., PDVI value) was found to change following the cardiac cycle. Images corresponding to $PDVI_{max}$ (bottom-left) and $PDVI_{min}$ (upper-right) were shown. The PDVI curve analyzed from 45 consecutive power Doppler images is shown in the bottom-right plot.

The renal blood flow analysis from power Doppler according to the invention was performed in four distinct regions of the kidney: the whole vascular tree, the interlobar vessels, the arcuate vessels and the interlobular vessels. The PDVI curves for individual region were plotted and the $PDVI_{max}$ of each curve was put close to each other (generally by ~30%) to facilitate the further comparison. The $PDVI_{max}$ and the $PDVI_{min}$ could be identified at these four PDVI curves (the whole vascular tree, the interlobar vessels, the arcuate vessels and the interlobular vessels) according to the changes at cardiac systole and diastole. These data could be saved for further statistical analysis by Excel when the curves were in regular pattern.

Figure 4A:
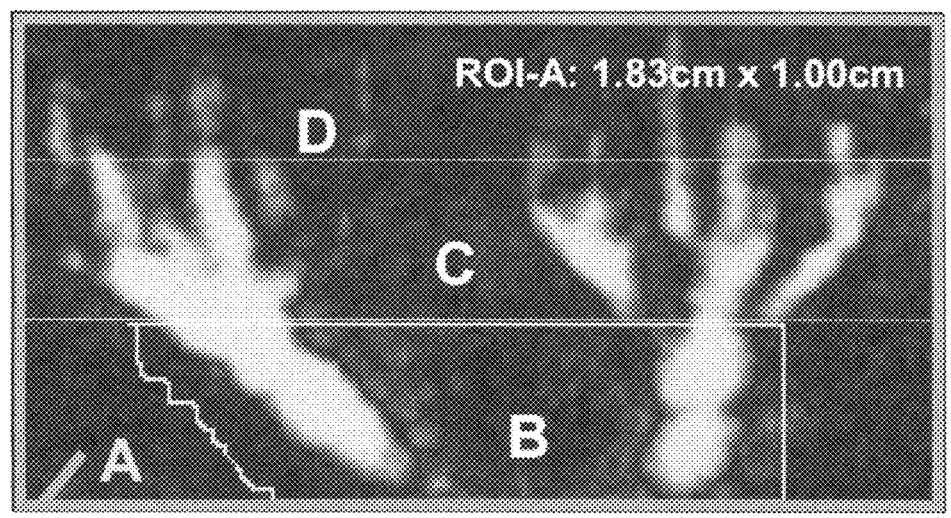
FIG. 4a shows the power Doppler vascular index (PDVI) analyzed for the four ROI selected in renal vascular tree.

FIG. 4a shows four typical areas of renal vessel selection for PDVI analysis: (A) the whole vascular tree, (B) interlobar, (C) arcuate, and (D) interlobular vessels.

Figure 4B:
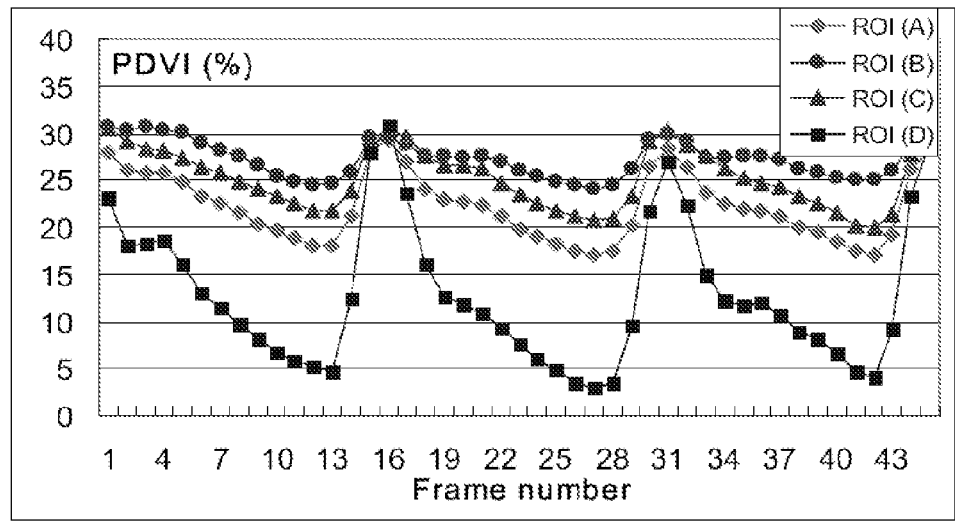
Figure 4C:
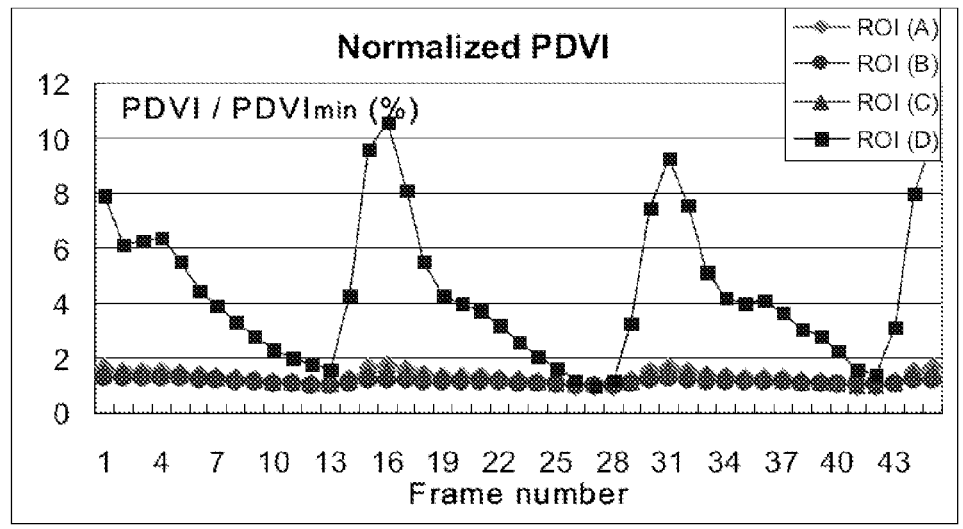
FIG. 4c shows normalized PDVI corresponding to four regions of FIG. 4b.

FIG. 4b shows the curves of power Doppler vascular index (PDVI) corresponding to four regions in FIG. 4a, i.e. the PVDI curves for each corresponding region. FIG. 4c shows the PDVI waveform normalized against its minimal value ($PDVI_{min}$) corresponding to four regions in FIG. 4b, which was similar to the systole/diastole ratio commonly used in hemodynamics for the evaluation of vascular perfusion. It was discovered that the change of the blood flow in the interlobular vessels is the most remarkable among these regions. Since renal function is mainly focused on the cortical glomerulus and the perfusion of the glomerulus comes from the interlobular vessels, the analysis on the interlobular vessels may represent the renal perfusion. Hence, the value of $PDVI_{max}/PDVI_{min}$ in this region is the first index for the analysis of renal perfusion.

The second index is a power Doppler index obtained by color weighting of PDVI with its brightness. Since the pixel brightness of the power Doppler ultrasonographic image in the ROI varied with the amount of the vascular perfusion, the pixel brightness of the image in the ROI can be divided by the maximal brightness of the power Doppler examination, and the ratio is defined as color-weighted power Doppler index (WPDVI). Then, an average for the sum of brightness ratios of all images is determined and the ratio is defined as mean color-weighted power Doppler index ($WPDVI_{mean}$) of the kidney, which serves as another evaluation index for renal vascular perfusion. The WPDVI is shown as follows:

$$WPDVI^k = \frac{1}{A_{ROI}} \cdot \sum_{i=1}^{nx} \sum_{j=1}^{ny} C_{i,j}^k \quad (2)$$

$$k = 1, N$$

where $C_{i,j}^k$ is the power Doppler scatter strength at the location (i, j) at the k-th frame.

Figure 5:
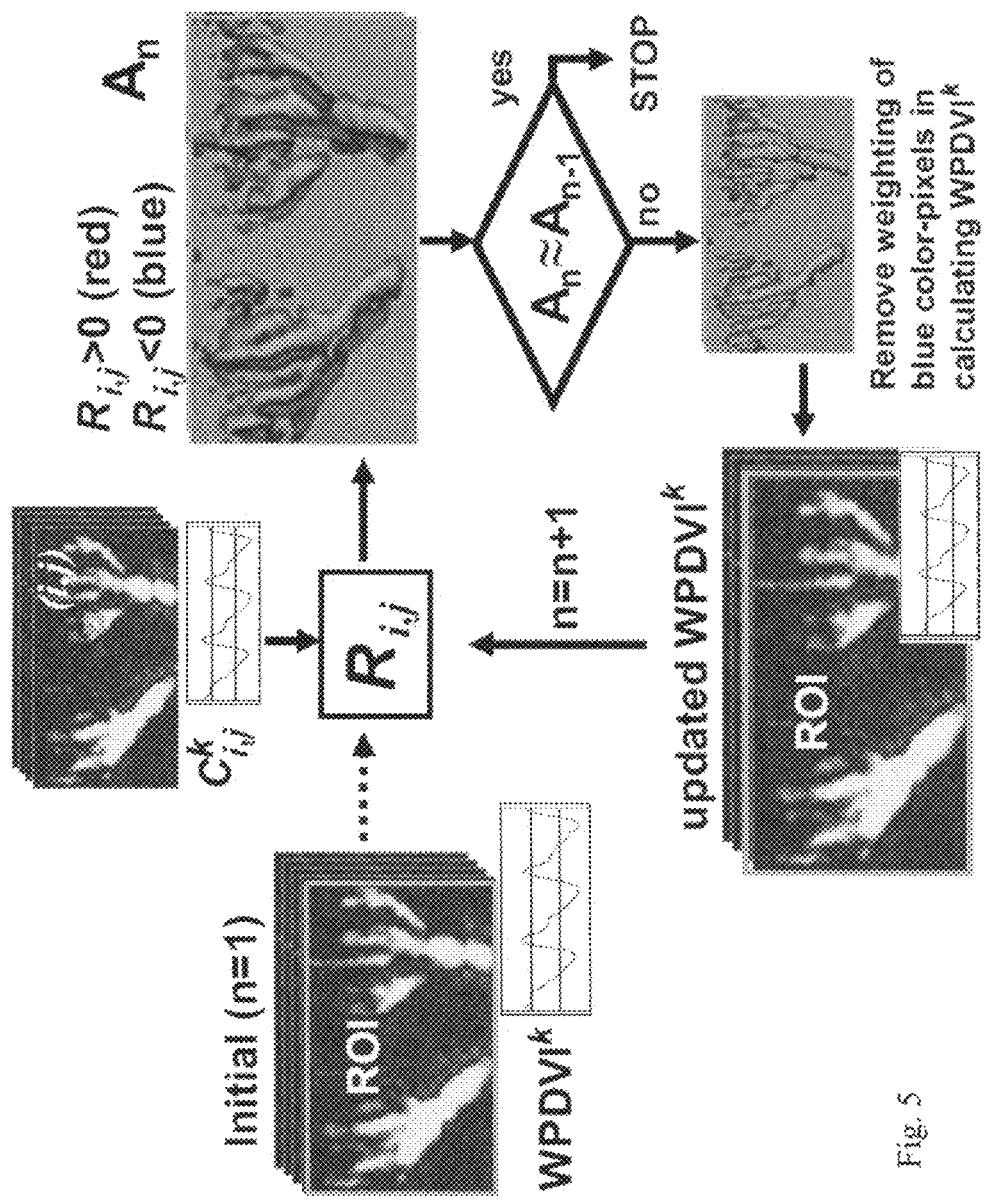
FIG. 5 shows the flow chart of the procedure for power Doppler correlation-map construction.

Referring to FIG. 5, it is the flow chart of the procedure for power Doppler correlation-map. The method used comprised the following steps: i) plotting a curve according to a color-weighted power Doppler vascularity index (WPDVI) and defining this waveform as an initial reference; ii) calculating a correlation matrix between the initial reference and the local waveform of scatter strength power; iii) defining pixels with positive correlation and negative correlation according to the calculation of the correlation matrix and marking them respectively with distinct colors to establish a power Doppler correlation-map; iv) eliminating pixels with negative correlation from the power Doppler correlation-map to serve as a reference for the next cycle; v) calculating again a correlation matrix between this reference and the local power Doppler scatter waveform at a given position.

The WPDVI waveform for those pixels with positive correlation and the WPDVI waveform for those pixels with negative correlation were marked with distinct colors to establish another power Doppler correlation-map. The iterative procedure was performed until the percentage of pixel-changes between the new power Doppler correlation-map ($A_n$) and the previous one ($A_{n-1}$) was less than a selected threshold. Areas with positive and negative correlation can be obtained respectively after relative comparisons.

From the hemodynamic point of view, the power Doppler waveform of the artery is different from the vein in pulsatility and in phase relationship. Different vascular structures can be differentiated through calibrated power Doppler strength over time. To achieve this object, the power Doppler strength of the color block was weighted in accordance with their brightness based on the WPDVI mentioned above. For initial reference (i.e., the first iteration n=1), the WPDVI waveform ($WPDVI^k$, k=1, N) of the original ROI was used to calculate the correlation matrix, $R_{i,j}$, with the local waveform of scatter strength ($C_{i,j}^k$, k=1,N at pixel (i, j)).

$$R_{i,j} = \frac{N \cdot \sum_{k=1}^{N} C_{i,j}^k \cdot WPDVI^k - \left[\sum_{k=1}^{N} C_{i,j}^k\right] \cdot \left[\sum_{k=1}^{N} WPDVI^k\right]}{\sqrt{N \cdot \sum_{k=1}^{N} (C_{i,j}^k)^2 - \left[\sum_{k=1}^{N} C_{i,j}^k\right]^2} \cdot \sqrt{N \cdot \sum_{k=1}^{N} (WPDVI^k)^2 - \left[\sum_{k=1}^{N} WPDVI^k\right]^2}} \quad (3)$$

Power Doppler correlation-map ($A_n$: image for the n-th iteration) was constructed using a neutral green background, the pixels with positive correlation ($R_{i,j}>0$) were marked red and pixels with negative correlation ($R_{i,j}<0$) were marked blue. The intensity of the red- or blue-color pixel represents the relative magnitude of correlation ($R_{i,j}$). For convenience, a maximum red- or blue-color intensity level of 100 was used in the 24-bits color image.

Since the initial power Doppler correlation-map ($A_n$; n=1) was drawn based on the WPDVI waveform that took all pixels of either positive or negative correlations into account, an iterative process was needed to purify the correlation-map with the reference-WPDVI waveform that associated with pixels of positive correlation only.

As indicated in the Figures, the reference-WPDVI waveforms ($WPDVI^k$, k=1, N) were iteratively updated, and the correlation matrix ($R_{i,j}$) between the WPDVI waveform and the local power Doppler scatter waveform ($C_{i,j}^k$, k=1,N) was re-calculated. The iterative procedure was performed until the percentage of pixel-changes between the new power Doppler correlation-map ($A_n$) and the previous one ($A_{n-1}$) was less than a selected threshold (for example: 1%).

Figure 6A:
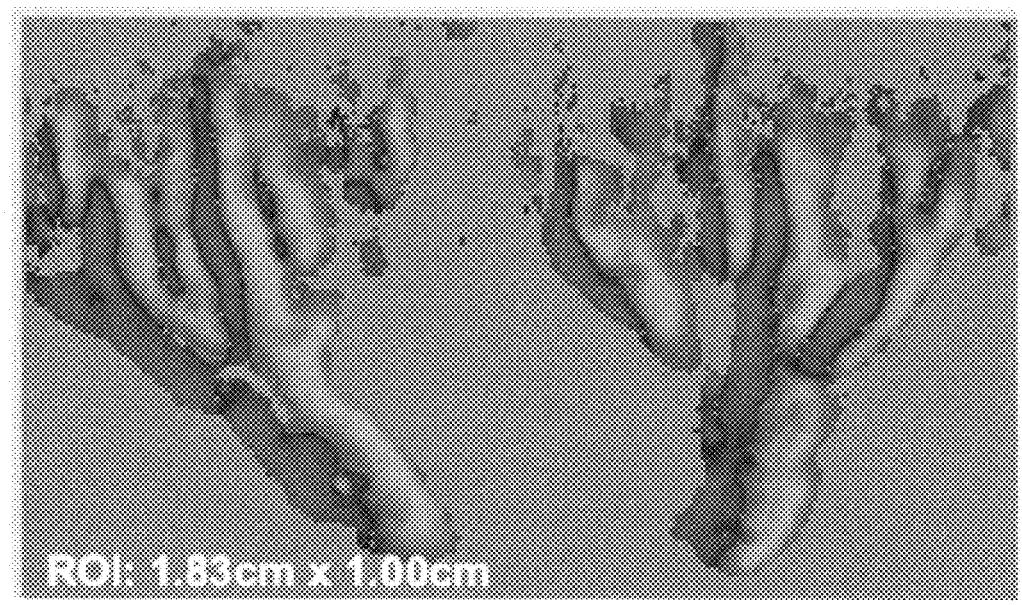
FIG. 6a shows converged results of a Power Doppler correlation-map, which can be classified into similar and dissimilar portions.
Figure 6B:
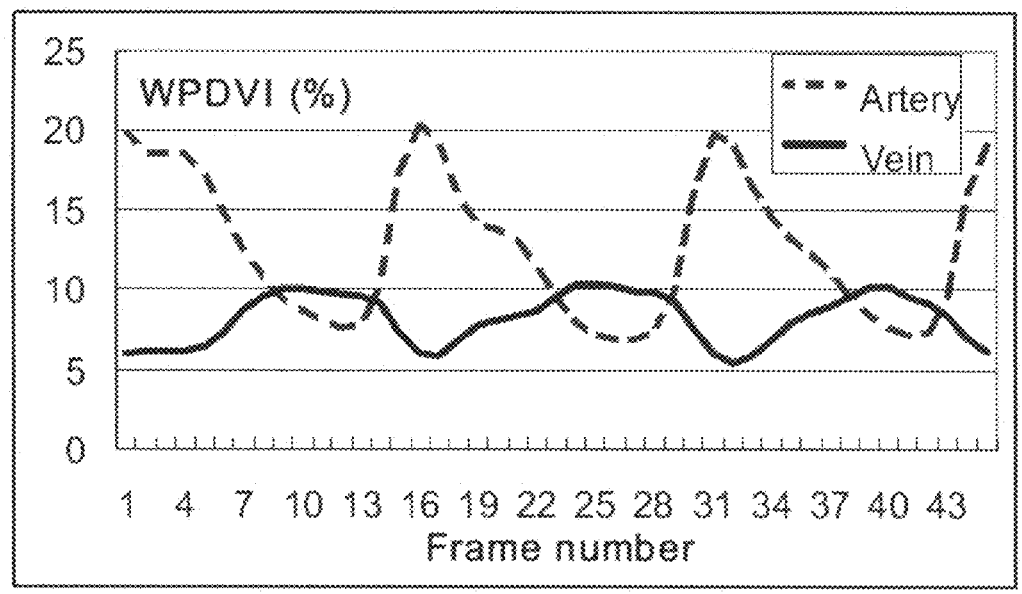
FIG. 6b shows waveforms of the color-weighted power Doppler vascular index (WPDVI) for pixels with both positive and negative correlations.

In general, the analysis of the correlation-map takes less than ten iterations to converge. Subsequently, the WPDVI waveforms of positive correlation (red pixel) and those of negative correlation (blue pixel) were calculated respectively. The converged results of the power Doppler correlation-map are shown in FIG. 6a, and the corresponding WPDVI waveforms for both positive (i.e., artery-like) and negative correlations (i.e., vein-like) are plotted on the same figure (FIG. 6b) for comparison. The arterial vessels generate a WPDVI waveform which is nearly opposite in phase with that of venous vessels. The color-weighted power Doppler flow signals generated by the arterial vessels (which are positively correlated with the overall WPDVI waveform) have higher fluctuating amplitude than those of the venous vessels. Separating the two vascular groups would have a lot of advantages in clinical applications such as tumor haemodynamics.

Table 1 shows the $PDVI_{min}$ and RVPI at the four renal vascular areas, namely (A) the whole vascular tree, (B) interlobar vessels, (C) arcuate vessels and (D) interlobular vessels, where the ROI were selected to give three different levels of PDVI$_{max}$ (i.e., about 20%, 30% and 40% respectively) for comparisons. As shown in Table 1, the values of RVPI (PDVI$_{max}$/PDVI$_{min}$) among various regions changed slightly although PDVI$_{min}$ varied with different PDVI$_{max}$ (20%, 30% and 40%). The interlobular vessel area had a maximal RVPI values and these values were more sensitive when compared to those in other regions. For example, the corresponding RVPI values were 9.81±0.73, 10.7±0.42 and 11.8±1.59 respectively when the PDVI$_{max}$ of the ROI-D was set at 20%, 30% and 40%; which were much higher than the values in other regions respectively. The blood flow in the interlobular vessel area showed a maximal change during cardiac contraction of systole and diastole. The RVPI value of the interlobular vessel area can therefore be used to define renal vascular perfusion, which can emphasize the dynamic vascular perfusion of terminal arteries before entering the glomerular capillaries and is highly representative.

TABLE 1

| ROI selection* | PDVI$_{max}$ | PDVI$_{min}$ | RVPI | p-value** |
|---|---|---|---|---|
| ROI-A (20%) | 20.8 ± 0.2 | 12.1 ± 0.1 | 1.72 ± 0.00 | <0.001 |
| ROI-B (20%) | 20.1 ± 0.2 | 15.6 ± 0.2 | 1.28 ± 0.01 | <0.001 |
| ROI-C (20%) | 19.8 ± 0.5 | 13.0 ± 0.3 | 1.52 ± 0.01 | <0.001 |
| ROI-D (20%) | 20.4 ± 0.5 | 2.1 ± 0.2 | 9.81 ± 0.73 | |
| ROI-A (30%) | 30.1 ± 0.6 | 17.6 ± 0.4 | 1.71 ± 0.02 | <0.001 |
| ROI-B (30%) | 30.7 ± 0.1 | 24.1 ± 0.1 | 1.28 ± 0.00 | <0.001 |
| ROI-C (30%) | 30.6 ± 0.3 | 20.1 ± 0.3 | 1.52 ± 0.01 | <0.001 |
| ROI-D (30%) | 30.4 ± 1.1 | 2.9 ± 0.1 | 10.7 ± 0.42 | |
| ROI-A (40%) | 40.2 ± 0.5 | 23.4 ± 0.3 | 1.73 ± 0.02 | <0.001 |
| ROI-B (40%) | 40.8 ± 0.7 | 31.8 ± 0.5 | 1.28 ± 0.00 | <0.001 |
| ROI-C (40%) | 40.6 ± 0.9 | 26.7 ± 0.6 | 1.52 ± 0.00 | <0.001 |
| ROI-D (40%) | 40.1 ± 1.2 | 3.4 ± 0.4 | 11.8 ± 1.59 | |

Table 2 shows the RVPI indices, the change in the values of PDVI$_{max}$/PDVI$_{min}$, at four renal vascular areas for the experiment on seven dogs. The four regions included (i) a region of the whole vascular tree, (ii) an interlobar vessel area, (iii) an arculate vessel area, and (iv) an interlobular vessel area. In all cases, the RVPI values for the interlobular vessels were significantly higher than those of the other three areas. Likewise, it was also proved that the analysis on the interlobular vessels could be representative for renal blood flow.

TABLE 2

| | NO. 1 | NO. 2 | NO. 3 | NO. 4 | NO. 5 | NO. 6 | NO. 7 |
|---|---|---|---|---|---|---|---|
| ROI-A | 1.72 ± 0.01 | 1.43 ± 0.03 | 1.81 ± 0.01 | 1.45 ± 0.00 | 1.74 ± 0.03 | 1.72 ± 0.00 | 1.55 ± 0.01 |
| p-value* | 0.0023 | 0.01 | <0.0001 | 0.00036 | 0.0002 | 0.00027 | 0.0013 |
| ROI-B | 1.34 ± 0.03 | 1.06 ± 0.001 | 1.11 ± 0.03 | 1.06 ± 0.01 | 1.28 ± 0.04 | 1.14 ± 0.02 | 1.18 ± 0.04 |
| p-value* | 0.0017 | 0.0087 | <0.0001 | 0.0003 | 0.00018 | 0.0002 | 0.001 |
| ROI-C | 1.44 ± 0.01 | 1.40 ± 0.04 | 1.53 ± 0.06 | 1.24 ± 0.02 | 1.25 ± 0.05 | 1.27 ± 0.08 | 1.42 ± 0.11 |
| p-value* | 0.0019 | 0.011 | <0.0001 | 0.00031 | 0.00019 | 0.0002 | 0.0015 |
| ROI-D | 6.71 ± 1.02 | 7.23 ± 2.01 | 5.81 ± .19 | 8.40 ± 0.76 | 5.51 ± 0.34 | 6.20 ± 0.45 | 6.57 ± 0.86 |

Figure 7:
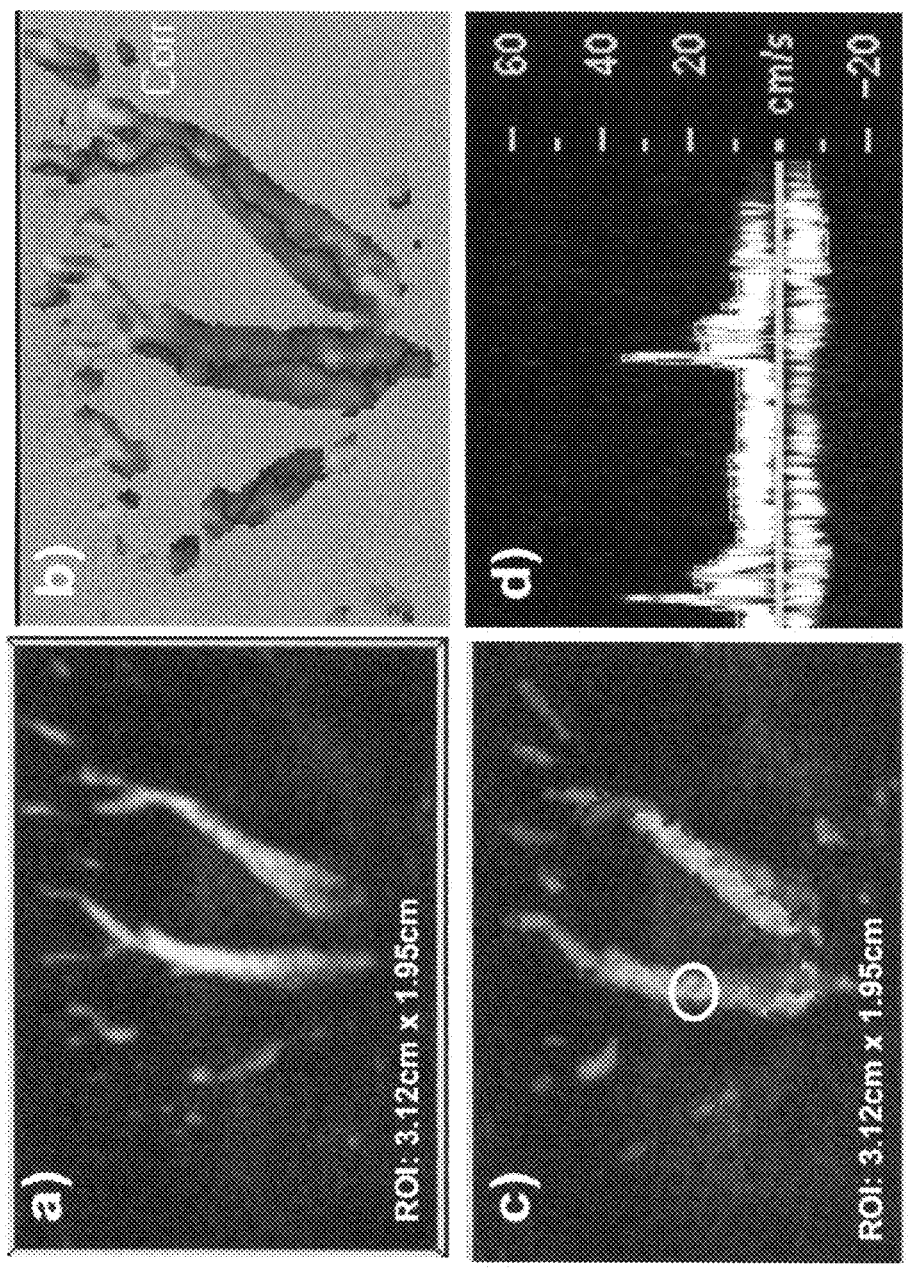
FIG. 7a shows the maximal power Doppler image of the kidney at systole.
FIG. 7b shows the power Doppler blood flow correlation-maps after calculation into two regions.
FIG. 7c shows color Doppler image of renal vessels with the renal arteries and veins.
FIG. 7d reveals a biphasic flow spectrum at the circled area of FIG. 7c, indicating the collateral structure of interlobar artery and vein respectively.

Refers to FIGS. 7a to 7d. FIG. 7a shows the maximal power Doppler image of the kidney at cardiac systole; FIG. 7b shows the power Doppler blood flow correlation-maps after calculation of 45 image frames; FIG. 7c shows color Doppler image of renal vessels with the renal arteries and veins. The region of the red pixels ($R_{i,j}>0$) in FIG. 7b corresponds to arteries and the region of the blue pixels ($R_{i,j}<0$) corresponds to veins. FIG. 7d is the image from pulse Doppler and which reveals a biphasic flow spectra at the circled area of FIG. 7c, indicating the collateral structure of interlobar artery and vein respectively. It has been proved that images in the power Doppler include the blood flow of arteries and veins.

Furthermore, it can be proved that the two indices can be used to evaluate renal vascular perfusion and renal function from the application of RVPI and WPDVI via clinical embodiments in the trials of animal and human.

Figure 8A:
FIGS. 8a and 8b reveal an improved renal perfusion after dopamine injection in an animal study.
Figure 8A:
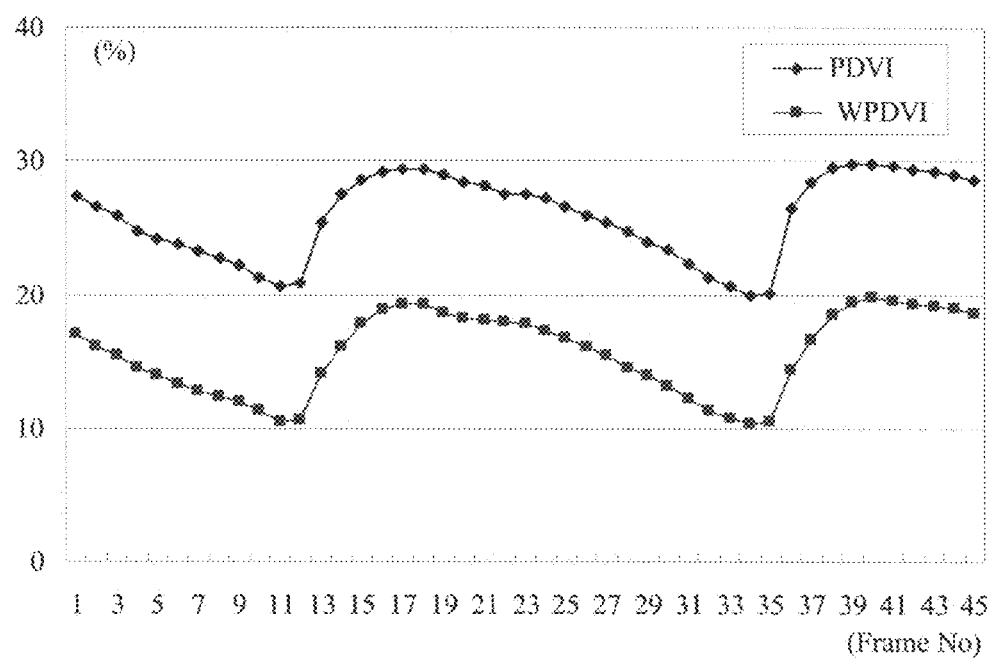
Figure 8B:
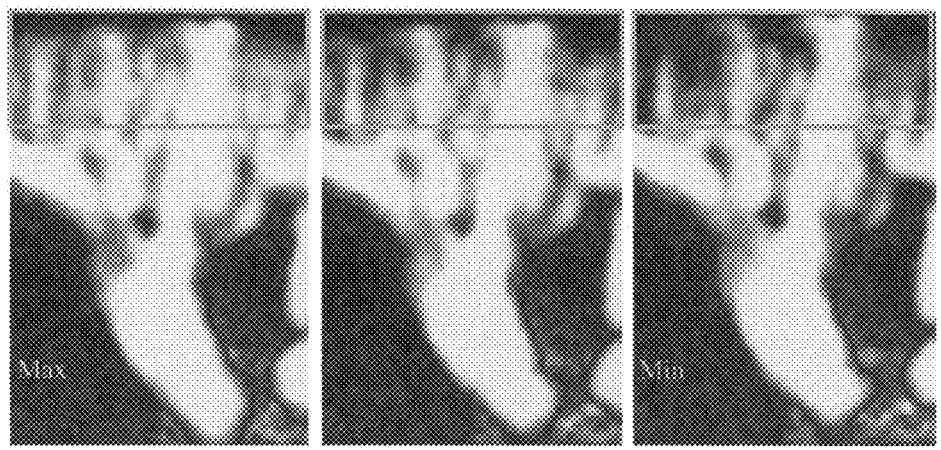
Figure 8B:
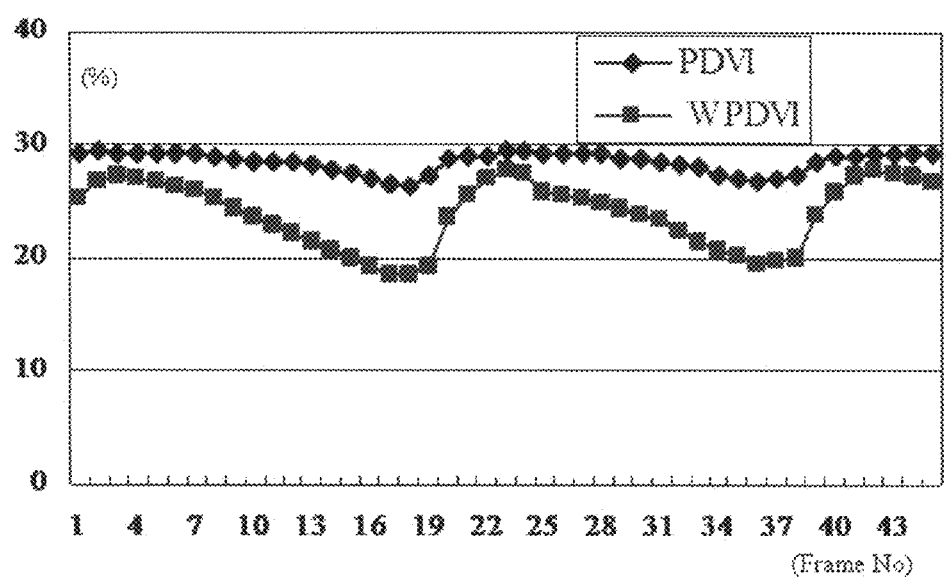

Referring to FIGS. 8a and 8b, the changes of renal vascular perfusion in dogs with dopamine infusion are shown. The images and plot prior to infusion are shown in FIG. 8a, while the images and plot following infusion are shown in FIG. 8b. Renal vascular perfusion in the interlobular vessel area was increased after intravenous infusion of dopamine, which could be observed from the images of blood flow (at the top of FIGS. 8a and 8b), and the decrease of PDVI as well as the change of WPDVI (at the bottom of FIGS. 8a and 8b). Referring to Table 3 at the same time, RVPI was decreased from 1.55 to 1.12, whereas WPDVI$_{mean}$ was increased from 15.1 to 21.6 after dopamine infusion.

Figure 9A:
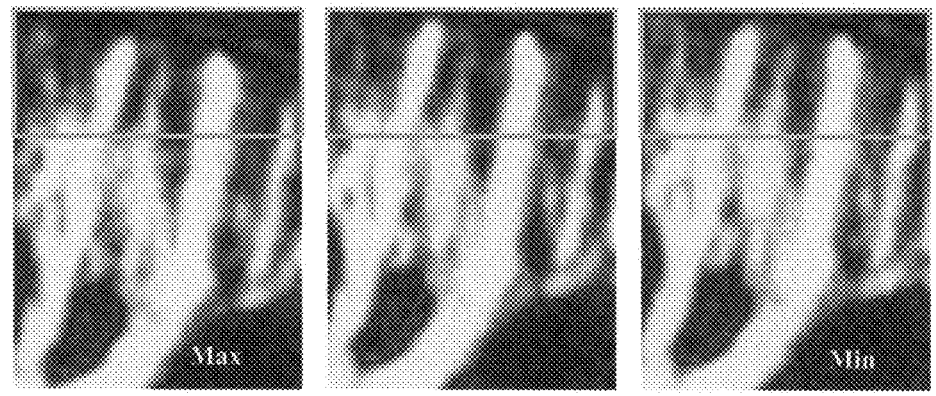
FIGS. 9a and 9b reveal impaired renal perfusion after experimental hydronephrosis produced by ureteral ligation in animal study.
Figure 9A:
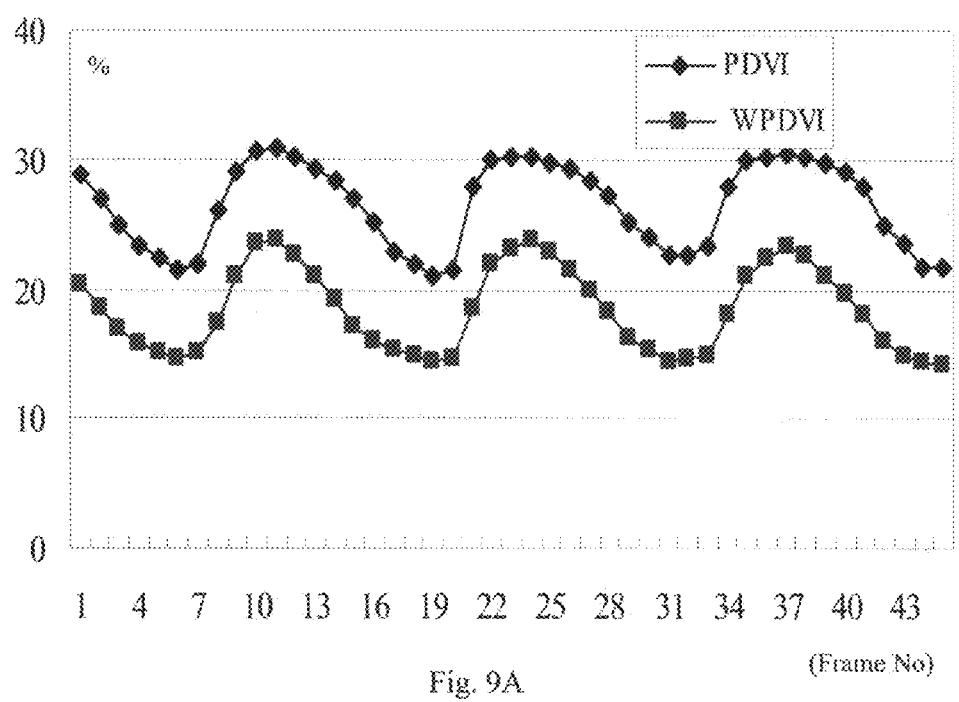
Figure 9B:
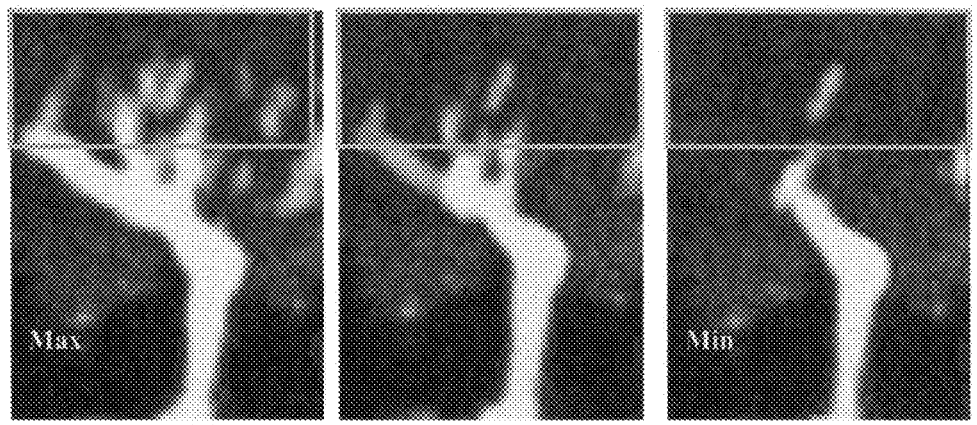
Figure 9B:
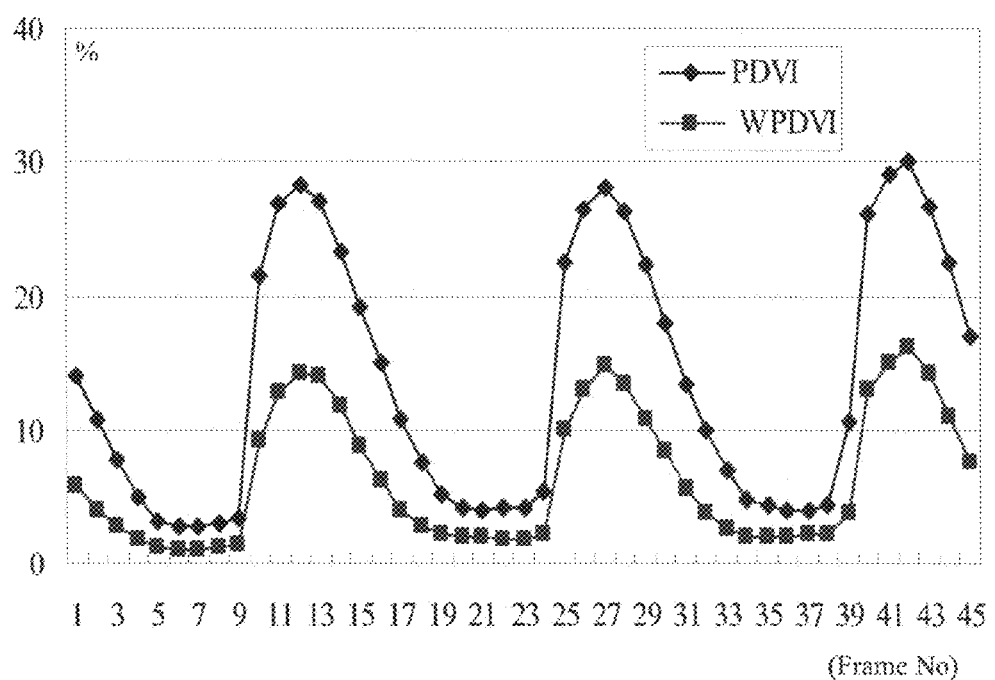

Referring to FIGS. 9a and 9b, the renal vascular perfusion before (9a) and after (9b) experimental hydronephrosis produced by ureteral ligation in animal study are shown. Renal blood flow in the interlobular vessel area decreased obviously (images at the top), while PDVI increased and WPDVI decreased (plots at the bottom) after ureteral ligation. As shown in Table 3, the RVPI was increased from 1.48 to 10.17 whereas WPDVI$_{mean}$ was decreased from 15.4 to 6.6 (3 days after ligation). However, renal vascular perfusion on the non-ligated side was not affected.

TABLE 3

| | interlobular vessels | | region of whole vascular tree | |
|---|---|---|---|---|
| | RVPI | WPDVImean | RVPI | WPDVImean |
| before dopamine infusion | 1.55 | 15.1 | 1.28 | 22.5 |
| after dopamine infusion | 1.12↓ | 21.6↑ | 1.07↓ | 27.9↑ |
| before ureteral ligation | 1.48 | 15.4 | 1.18 | 23.7 |
| 3 days after ureteral ligation | 10.17↑ | 6.6↓ | 2.84↑ | 15.8↓ |
| 6 days after ureteral ligation | 4.47↑ | 9.5↓ | 2.61↑ | 14.1↓ |

TABLE 3-continued

| | interlobular vessels | | region of whole vascular tree | |
|---|---|---|---|---|
| | RVPI | WPDVImean | RVPI | WPDVImean |
| 8 days after ureteral ligation | — | — | 3.34↑ | 14.3↓ |
| non-ligated side of ureter | 1.53 | 15.4 | 1.16 | 27.6 |

Referring to FIGS. 10a to 10f, various statuses of renal perfusion in patients after renal transplantation were shown.

Figure 10A:
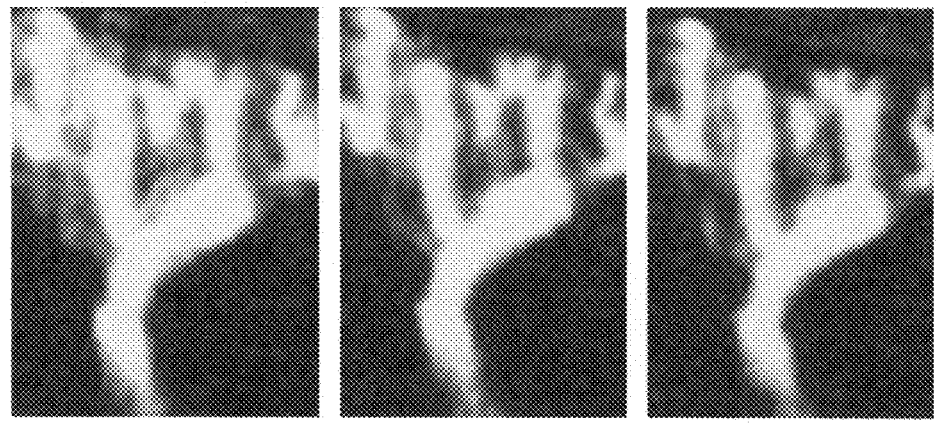
Figure 10A:
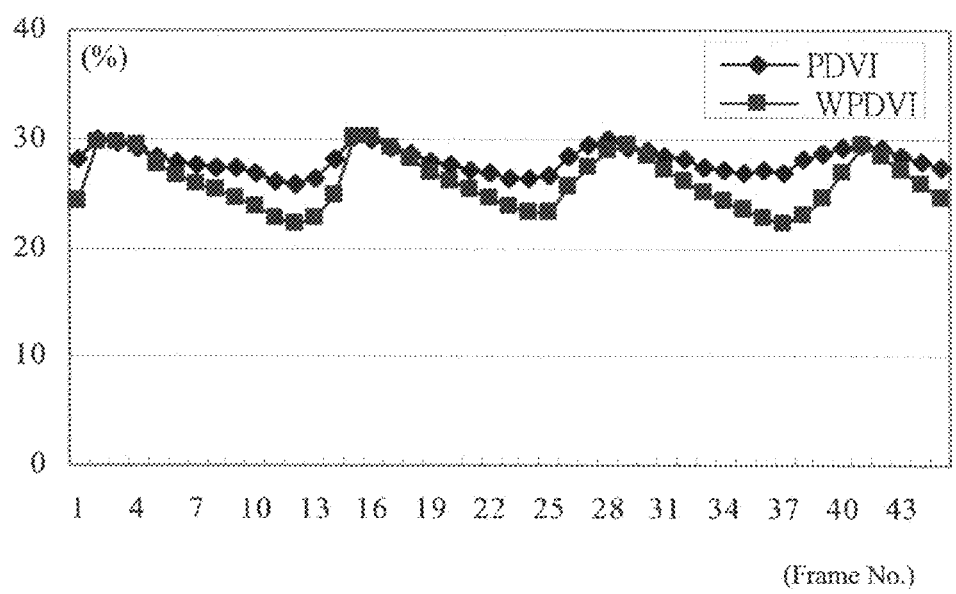
Figure 10B:
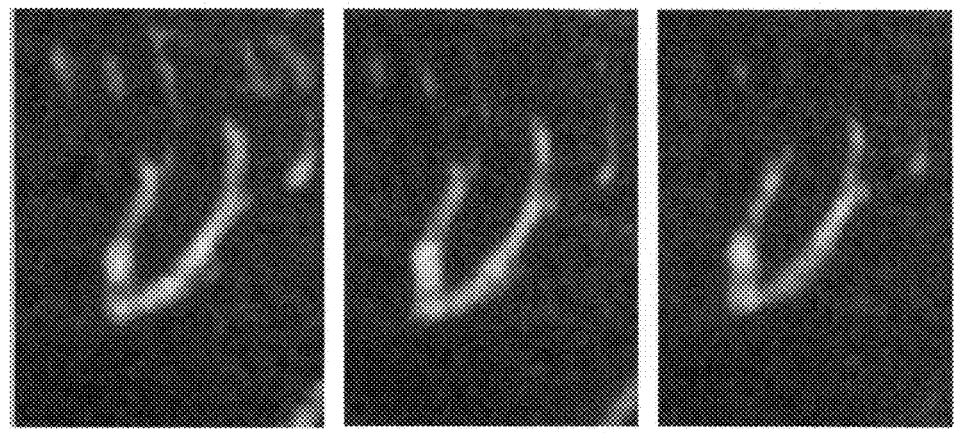
Figure 10B:
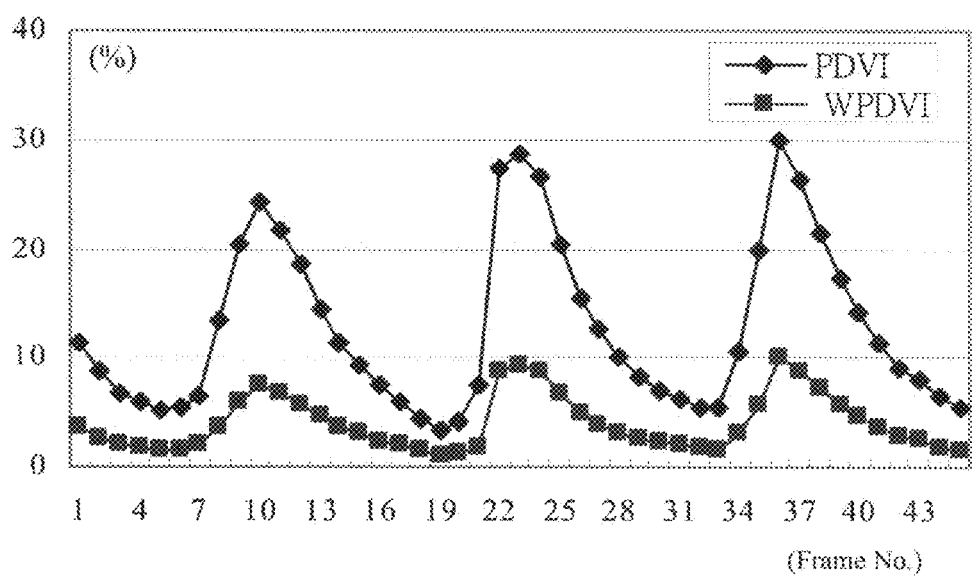
Figure 10C:
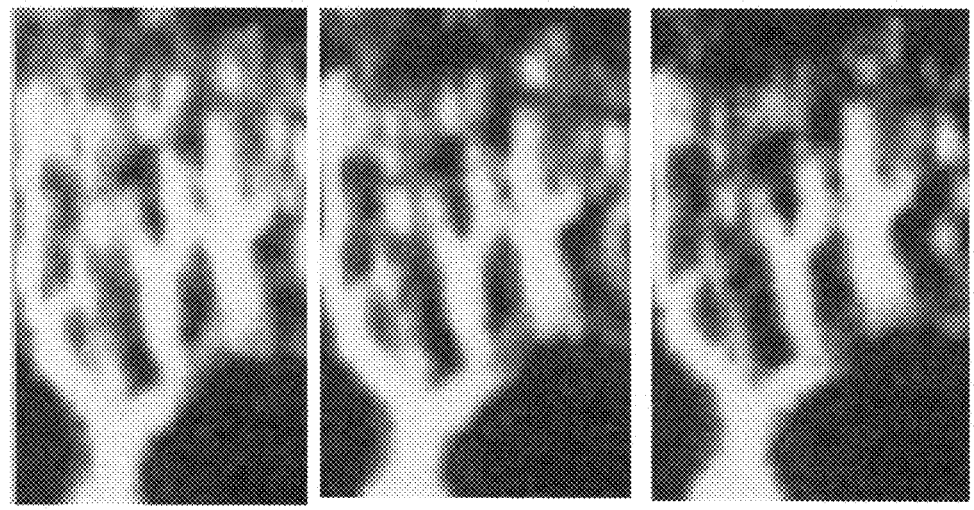
Figure 10C:
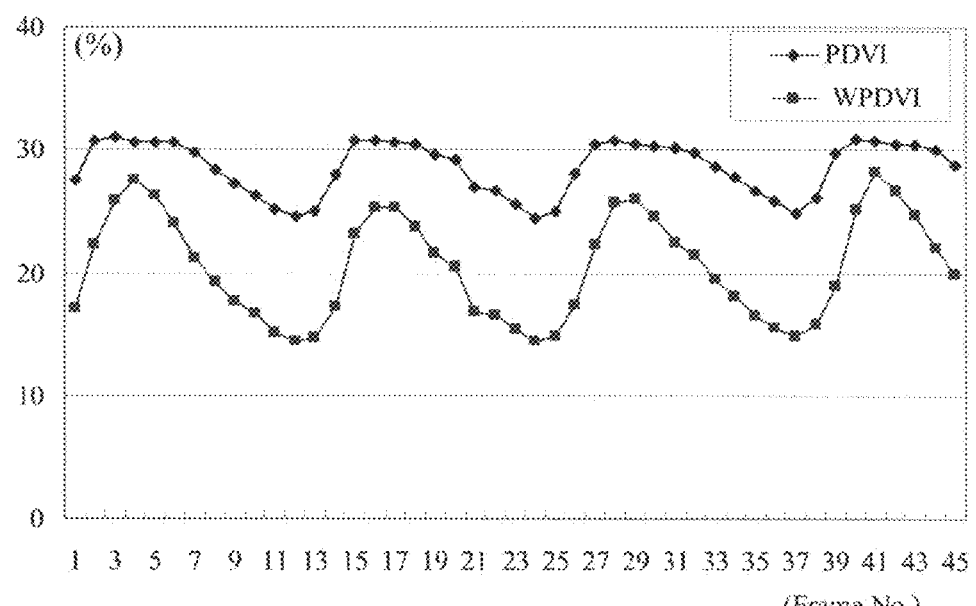
Figure 10D:
Figure 10D:
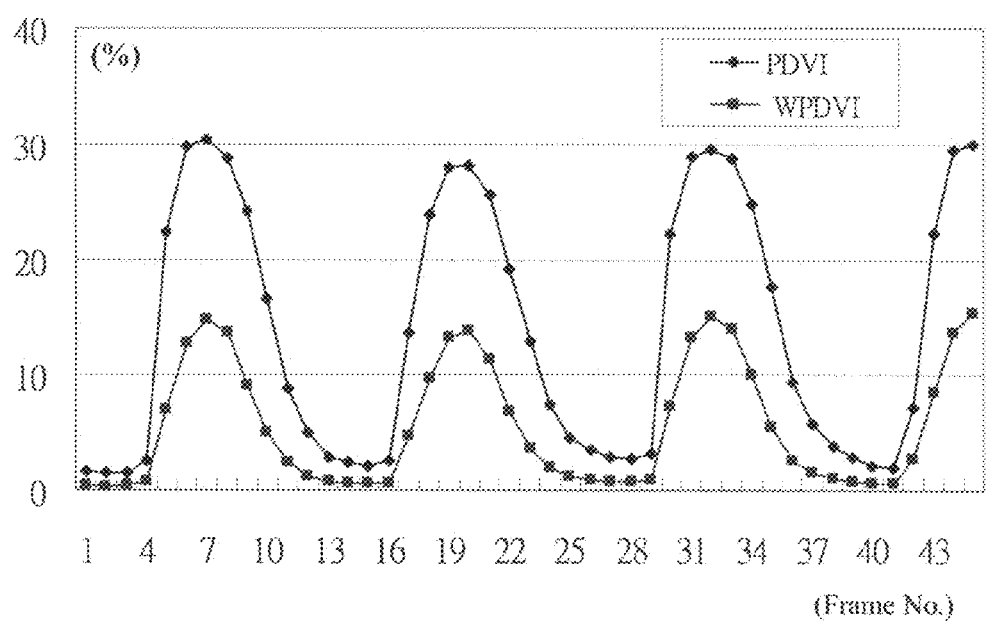
Figure 10F:
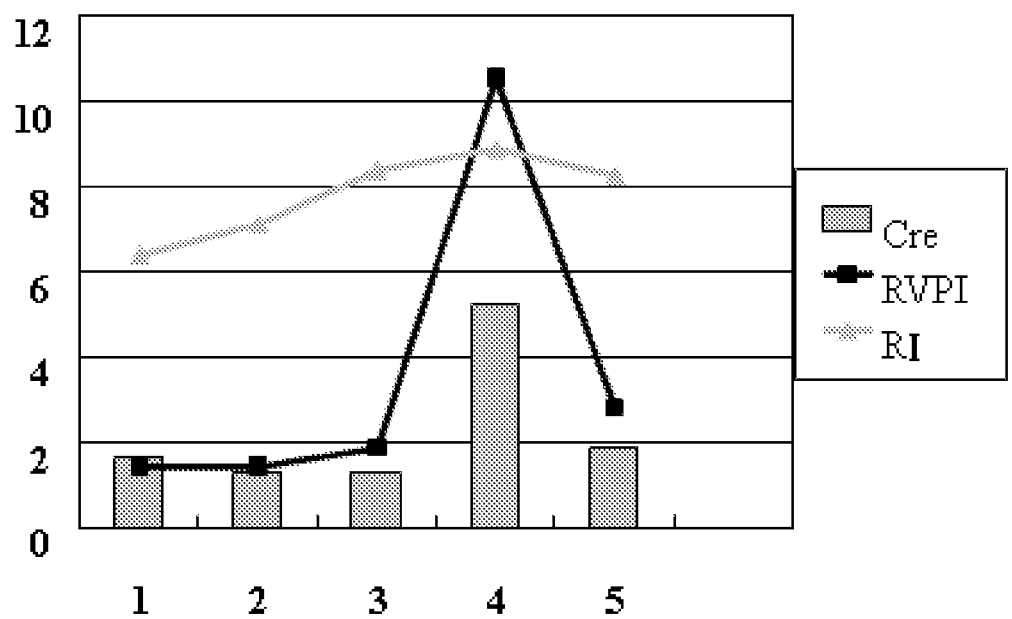

The values of RVPI and WPDVI$_{mean}$ were summarized in Table 4. Good renal perfusion in patient A after renal transplantation was shown in FIG. 10*a*. The RVPI and the WPDVI$_{mean}$ value of the interlobular vessel area was 1.2 and 24.8 respectively (Table 4). FIG. 10*b* revealed a poor status of renal perfusion in patient B after renal transplantation, with an RVPI value of 14.7 and a WPDVI$_{mean}$ value of 3.3 in the interlobular vessel area (Table 4). FIG. 10*c* showed a good status for renal perfusion in the patient C at 10 days after renal transplantation, with an RVPI value of 1.33 and a WPDVI$_{mean}$ value of 18.3 in the interlobular vessel area (Table 4). Worse renal perfusion was found in patient C at 52 days after renal transplantation due to acute rejection (FIG. 10*d*), with an RVPI value of 27.4 and a WPDVI$_{mean}$ value of 5.3 in the interlobular vessel area (Table 4). An improved renal perfusion was shown in patient C at 80 days after renal transplantation when the acute rejection was treated (FIG. 10*e*), with an RVPI value of 1.57 and a WPDVI$_{mean}$ value of 18.5 in the interlobular vessel area (Table 4). FIG. 10*f* showed a correlation between the renal function index (Creatinine) and the RVPI value in patient C. RVPI increased with elevated creatinine level, which was resulted from renal dysfunction after acute rejection. Similarly, RVPI decreased when creatinine level was declined. Change in RVPI was found on the third examination when creatinine level was not evidently changed. This indicated RVPI could predict a change in advance. In addition, the commonly used resistive index (RI) was found to be not as sensitive as RVPI.

TABLE 4

|  | interlobular vessels | | region of whole vascular tree | |
| --- | --- | --- | --- | --- |
|  | RVPI | WPDVI$_{mean}$ | RVPI | WPDVI$_{mean}$ |
| good vascular perfusion in patient A | 1.2 | 24.8 | 1.1 | 27.3 |
| poor vascular perfusion in patient B | 14.7↑ | 3.3↓ | 2.45↑ | 5.34↓ |
| good vascular perfusion in patient C | 1.33 | 18.3 | 1.17 | 24.6 |
| poor blood flow due to acute rejection in patient C | 27.4↑ | 5.3↓ | 3.15↑ | 11.1↓ |
| improved vascular perfusion in patient C | 1.57 | 18.5 | 1.21 | 22.9 |

Table 4 showed renal perfusion parameters RVPI and WPDVI$_{mean}$ values at the interlobular vascular and the whole vascular trees for patients after kidney transplantation. The evaluation of renal transplant perfusion in patients (from good to poor) could be correlated with the variation of RVPI and WPDVI$_{mean}$ in both the interlobular vessels and the whole vascular trees.

RVPI and WPDVI$_{mean}$ in the invention are shown to be 2 useful parameters from Table 3 and Table 4. Lower RVPI (in the range of 1 to 1.5) and higher WPDVI$_{mean}$ reflected good kidney condition, while higher RVPI (greater than 2) and lower WPDVI$_{mean}$ (30% to 72% less than normal value, WPDVI$_{mean}$ is preferably less than 10) showed a poor condition. On the other hand, the poor renal vascular perfusion might cause the PDVI$_{min}$ in the interlobular vessel area to be zero, which resulted in difficulties for the calculation of RVPI and WPDVI. As a result, analysis in the demarcated region of whole vascular tree was developed. According to the results, this method could be also used for the analysis of poor renal perfusion in ureteral ligation study (Table 3). As shown in Table 3, the interlobular vessel area could not be analyzed eight days after ureteral ligation. However, the increase in RVPI and the decrease in WPDVI$_{mean}$ at the region of whole vascular tree can be taken for analysis.

Up to present, the potential in clinical practice and research of the power Doppler are still improving, in particular to the structure of irregular vasculature. Technically, the pulsations in arteries and veins need to be differentiated. The present invention not only demonstrated the renal PDVI to pulsate over the cardiac cycle but also to correlate the color-weighted WPDVI waveform to the haemodynamics of renal vessels using a power Doppler correlation-map. Although the indices used in the present invention resembled the systole/diastole (S/D) ratio that is commonly used to quantify arterial resistance or arterial vascular perfusion hemodynamically, the systole/diastole (S/D) ratio known in the prior art was carried out in a one-dimensional manner using pulsed Doppler examination, which is merely suitable for observation of renal interlobar arterial velocity and vascular resistance. The present invention relies principally on observation of all blood flow in the renal cortex, where the dynamic analysis on vascular perfusion is performed in a two-dimensional manner. This will be of great benefit for long-term observation in patients with chronic renal disease.

Although the present invention has been already disclosed by referring to foregoing preferable embodiments and persons skilled in the art might easily make some alterations or modifications by this, this will not depart from the scope defined by the claims of the present invention.

What is claimed is:

1. A method for the evaluation of renal perfusion and renal function with power Doppler ultrasonography comprising the steps of:
    (i) using a Power Doppler ultrasound and consecutively capturing serial images on kidney for at least two complete heartbeat cycles and respectively selecting a region of interest (ROI) from a plurality of ROIs, wherein the ROI corresponds to an image in the serial images;
    (ii) demarcating pixels showing reflected signals of blood flow in each ROI;
    (iii) within the ROI of each image in the serial images, calculating a ratio through dividing an area by a total area in the ROI to yield a power Doppler vascularity index (PDVI), wherein the area is summed by the pixels showing reflected signals of blood flow;
    (iv) in all the PDVI of the serial images, taking a maximum PDVI to be divided by a minimum PDVI to yield a renal vascular perfusion index (RVPI);
    (v) within the ROI of each image in the serial images, obtaining a plurality of normalized pixels through dividing a brightness of each pixel by a maximal brightness; for each image within the serial images, summing the brightness of all the plurality of normalized pixels in the ROI to yield a plurality of color-weighted power Doppler vascularity index (WPDVI), and by working through the serial images, getting a sequence of WPDVIs;
    (vi) averaging all of the WPDVI values to yield a mean color-weighted power Doppler vascularity index (WPDVI$_{mean}$); and, (vii) using the RVPI and the $\text{WPDVI}_{mean}$ to evaluate renal vascular perfusion and renal function.

2. The method as claimed in claim 1, wherein the ROI is selected from the group consisting of an interlobular vessel area, an arcuate vessel area, and an interlobar vessel area.

3. The method as claimed in claim 1, wherein the ROI is a whole renal vascular tree consisting of an interlobular vessel area, an arcuate vessel area, and an interlobar vessel area.

4. The method as claimed in claim 1, wherein if the RVPI is greater than 2 and the $\text{WPDVI}_{mean}$ is lower than 10, then it is predictive of deteriorating renal vascular perfusion.

5. The method as claimed in claim 1, wherein if the RVPI is in the range of 1.01-2, then it is predictive of normal renal vascular perfusion.

6. A method for evaluation of renal perfusion comprising the steps of:
(i) capturing serial images on kidney with two-dimensional power Doppler ultrasonography, and selecting a region of interest (ROI) from a plurality of ROIs, wherein the ROI corresponds to an image in the serial images;
(ii) within the ROI of each image in the serial images, calculating a ratio through dividing an area by a total area in the ROI to yield a power Doppler vascularity index (PDVI), wherein the area is summed by the pixels showing reflected signals of blood flow and taking a maximum PDVI to be divided by a minimum PDVI to yield a renal vascular perfusion index (RVPI);
(iii) within the ROI of each image in the serial images, obtaining a plurality of normalized pixels through dividing a brightness of each pixel by a maximal brightness; for each image within the serial images, summing the brightness of all the plurality of normalized pixels in the ROI to yield a plurality of color-weighted power Doppler vascularity index (WPDVI), and by working through the serial images, getting a sequence of WPDVIs, and calculating the mean of the sequence of WPDVIs; and
(iv) using the RVPI and the $\text{WPDVI}_{mean}$ to evaluate renal vascular perfusion.

7. The method as claimed in claim 6, wherein the ROI is selected from the group consisting of an interlobular vessel area, an arcuate vessel area, and an interlobar vessel area.

8. The method as claimed in claim 6, wherein the ROI is a whole renal vascular tree consisting of an interlobular vessel area, an arcuate vessel area, and an interlobar vessel area.

9. The method as claimed in claim 6, wherein if the RVPI is greater than 2 and the $\text{WPDVI}_{mean}$ is lower than 10, then it is predictive of deteriorating renal vascular perfusion.

10. The method as claimed in claim 6, wherein if the RVPI is in the range of 1.01-2, then it is predictive of normal renal vascular perfusion.

11. The method as claimed in claim 6, wherein the steps after step (iii) further include establishing a first power Doppler correlation-map and a second power Doppler correlation-map to differentiate various vascular structures, which comprise:
(a) plotting a curve according to a color-weighted power Doppler vascularity index (WPDVI) and defining this waveform as an initial reference;
(b) using an equation for calculating a first correlation matrix between the initial reference and a local waveform of scatter strength at the ROI; and
(c) defining pixels with positive correlation and negative correlation according to the calculation of the first correlation matrix and marking them respectively with distinct colors to establish the first power Doppler correlation-map, and the colors stand for different vascular structures respectively;

wherein the equation is represented by $$R_{i,j} = \frac{N \cdot \sum_{k=1}^{N} C_{i,j}^k \cdot WPDVI^k - \left[\sum_{k=1}^{N} C_{i,j}^k\right] \cdot \left[\sum_{k=1}^{N} WPDVI^k\right]}{\sqrt{N \cdot \sum_{k=1}^{N} (C_{i,j}^k)^2 - \left[\sum_{k=1}^{N} C_{i,j}^k\right]^2} \cdot \sqrt{N \cdot \sum_{k=1}^{N} (WPDVI^k)^2 - \left[\sum_{k=1}^{N} WPDVI^k\right]^2}}$$

wherein the waveform of WPDVI ($WPDVI^k$, k=1, N), the local waveform of scatter strength ($C_{i,j}^k$, k=1,N at pixel (i, j)).

12. The method as claimed in claim 11, wherein further steps after the step (c) comprise:
(I) eliminating pixels with negative correlation from the first power Doppler correlation-map to serve as a second reference;
(II) calculating again a second correlation matrix between the second reference and the local waveform of scatter strength at the ROI; and
(III) defining pixels with positive correlations and negative correlations according to calculation of the second correlation matrix and marking the pixels with distinct colors to establish the second power Doppler correlation-map.

13. The method as claimed in claim 12, wherein further steps after the step (III) comprise: comparing the first power Doppler correlation-map with the second power Doppler correlation-map, repeating step (I) when the ratio of change in the pixels of the first power Doppler correlation-map and the second power Doppler correlation-map exceeds a selected threshold.

* * * * *